United States Patent [19]

Stuerzebecher et al.

[11] Patent Number: 5,607,937
[45] Date of Patent: Mar. 4, 1997

[54] PIPERAZIDES OF SUBSTITUTED PHENYLALANINE DERIVATIVES AS THROMBIN INHIBITORS

[75] Inventors: Joerg Stuerzebecher, Erfurt-Rhoda; Helmut Vieweg, Rheinfelden, both of Germany; Peter Wikstroem, Oberwil; Christoph Adler, Reinach, both of Switzerland

[73] Assignee: Pentapharm AG, Basel, Switzerland

[21] Appl. No.: 318,649

[22] PCT Filed: Feb. 9, 1994

[86] PCT No.: PCT/CH94/00026

§ 371 Date: Jan. 5, 1995

§ 102(e) Date: Jan. 5, 1995

[87] PCT Pub. No.: WO94/18185

PCT Pub. Date: Aug. 18, 1994

[30] Foreign Application Priority Data

Feb. 10, 1993 [CH] Switzerland ............................ 405/93
Sep. 20, 1993 [CH] Switzerland ........................... 2827/93

[51] Int. Cl.$^6$ .................. C07D 295/192; C07D 401/04; C07D 403/04; A61K 31/495
[52] U.S. Cl. ..................... 514/255; 544/387; 544/391; 544/360; 544/295; 544/121; 544/376; 544/380
[58] Field of Search .................... 544/387, 391, 544/360, 295, 121, 376, 380; 514/255

[56] References Cited

FOREIGN PATENT DOCUMENTS

0097630A3  1/1984  European Pat. Off. .
92/08709   5/1992  WIPO .

*Primary Examiner*—Mukund J. Shah
*Assistant Examiner*—King Lit Wong
*Attorney, Agent, or Firm*—Pennie & Edmonds

[57] ABSTRACT

The present invention relates to D,L-, L- and D-phenylalanine piperazides of formula (I) defined in claim 1 that inhibit blood coagulation, and thrombin and/or trypsin, respectively. The compounds are extraordinarily absorbable after oral, intraduodenal and in particular rectal administration and show only a low toxicity.

19 Claims, No Drawings

PIPERAZIDES OF SUBSTITUTED PHENYLALANINE DERIVATIVES AS THROMBIN INHIBITORS

This application is the national stage of PCT/CH94/00026, filed Feb. 9, 1994.

The present invention relates to new proteinase inhibitors which contain phenylalanine as the core structure, wherein the aromatic residue in meta position carries a basic group and the a-amino group is sulfonylated with various residues. The C-terminal introduction of different, N-substituted piperazine residues led to the discovery of highly efficient inhibitors showing improved bioavailability.

Proteinase inhibitors are potential drugs which can be used to control physiological processes induced and maintained by proteinases. For many endogenous and naturally occurring inhibitors, respectively, it has been shown that they can influence the activity of proteinases in vivo and alleviate hyperproteolytic states [see Hörl, W. H. In: Design of Enzyme Inhibitors as Drugs, p. 573–581, (Sandler, M. and Smith, H. J., Eds.) Oxford, New York, Tokyo: Oxford University Press, 1989]. However, the therapeutic application of such inhibitors of relatively high molecular weight is limited due to their particular protein structure. As these inhibitors are not absorbed in the intestine upon oral administration on the one hand and exert an antigenic activity on the other hand, it was of great interest to search for synthetic enzyme inhibitors of low molecular weight.

The four classes of enzymes which are responsible for proteinase-dependent processes comprise the serine, thiol, metallo, and aspartate proteinases. Serine proteinases are proteolytic enzymes which possess a reactive serine residue in the active center. Enzymes which, such as trypsin, split off C-terminal peptide bonds of the basic amino acids arginine and lysine, belong to the trypsin family of the serine proteinases. In this group, those enzymes which induce coagulation and fibrinolysis in the blood, which release kinin and produce the complement activation or those which themselves are components of the mentioned enzyme systems, are of particular physiological significance.

Blood coagulation is triggered by zymogen activation via two different pathways. The first, intrinsic pathway leads to blood coagulation via a chain of reactions mediated by blood constituents. The second, extrinsic pathway leads to coagulation via a shorter chain of reactions based on an interaction between blood and tissue constituents. Both ways produce the activation of the zymogen factor X into the serine proteinase factor $X_a$ which itself catalyzes the activation of prothrombin into the fibrinogen-coagulating serine proteinase, thrombin. Being a common product of the intrinsic as well as of the extrinsic activation pathway, factor $X_a$ was initially considered to be the preferential target enzyme for inhibitory intervention in the blood coagulation process (Tidwell, R. R. et al., Thromb. Res. 19, 339–349, 1980). However, it has been recently demonstrated that synthetic inhibitors of factor $X_a$ in vitro and in vivo are not coagulation-inhibiting (Stürzebecher, J. et al., Thromb. Res. 54, 245–252, 1989) and antithrombotically efficient (Hauptmann, J. et al., Thromb. Haemostas. 63, 220–223, 1990). Therefore, the development of anticoagulant inhibitors is focused on the discovery of thrombin inhibitors.

For the development of synthetic inhibitors for thrombin, benzamidine derivatives have been extensively investigated (Stürzebecher, J. et al., Acta Biol. Med. Germ. 35, 1665–1676, 1976). Among them, amino acid derivatives containing a benzamidine moiety and a para-oriented amidino group proved to be favorable core structures for the development of effective inhibitors. Until now, the most efficient thrombin inhibitor of the benzamidine type described is the amino acid derivative Nα-(2-naphthylsulfonyl)-glycyl-4-amidinophenylalanine piperidide (NAPAP) ($K_i=6\times10^{-9}$ mol/l) (Stürzebecher, J. et al., Thromb. Res. 29, 635–642, 1983).

Other types of inhibitors which also effectively inhibit thrombin are known: a first group is comprised of the peptidyl-arginine-chloromethyl ketones, e.g. H-D-Phe-Pro-Arg-CH$_2$Cl (Kettner, C. et al., Thromb. Res. 14, 969–973, 1979). A second group is comprised of the peptidylarginine aldehydes, e.g. Boc-D-Phe-Pro-Arg-H and H-D-Phe-Pro-Arg-H (Bajusz, S., Int. J. Peptide Protein Res. 12, 217–221, 1978).

However, these inhibitors which inhibit trypsin and thrombin with a comparable affinity are not easily synthesized, are unstable and may cause undesired side reactions due to their high reactive capacity. Thrombin, and trypsin as well, are inhibited in a time-dependent reaction by the boronic acid derivative Boc-D-Phe-Pro-Boro-Arg-C$_{10}$H$_{16}$ (see European Patent Application No. 0 293 881). Conversely, the selective thrombin inhibitor (2R,4R)-4-methyl-1-[Nα-(3-methyl-1,2,3,5-tetrahydro-8-quinolinesulfonyl)-L-arginine]-2-pipecoline-carboxylic acid has practically no trypsin-inhibiting activity (Kikumoto, R. et al., Biochemistry 23, 85–90, 1984).

All the benzamidine derivatives investigated until now possess pharmacodynamic and pharmacokinetic properties which make them unfavorable for a therapeutic application. Upon oral application they are not absorbed in the intestine, they are quickly eliminated from the circulation and their toxicity is relatively high. This applies to the amides of the N-α-arylsulfonylated (Markwardt, F. et al., Thromb. Res. 17, 425–431, 1980) as well as to amides of the N-α-arylsulfonylaminoacylated 4-amidinophenylalanine (see Patent Application No. DD-A-235 866). The responsibility for the inadequate pharmacological properties is attributable to the strongly basic amidino function (Kaiser, B. et al., Pharmazie 42, 119–121, 1987). Experiments aimed at replacing the strongly basic amidino function in highly effective inhibitors by less basic groups first failed as they resulted in a significant loss in efficacy (Stürzebecher, J. et al., Pharmazie 43, 782–783, 1988). Also, the introduction of a carboxyl group in the inhibitor to reduce the basicity of the amidino function led to a decrease in the inhibitory activity. Thus, derivatives of the 4-amidinophenylalanine which possess a C-terminal amino acid with a free carboxyl group are fully ineffective as inhibitors (Wagner, G. et al., Pharmazie 39, 16–18, 1984; Vieweg, H. et al., Pharmazie 39, 82–86, 1984).

The modification of NAPAP by the introduction of a substituent at the α-nitrogen led to a slight increase in the antithrombin activity (see European Patent Application No. FR-A-2 593 812), neither improved the pharmacological properties (Cadroy, Y. et al., Thromb. Haemostas. 58, 764–767, 1987).

Starting from Nα-substituted 3-amidinophenylalanine, the development of selective thrombin inhibitors was continued; it has been found that amides of the Nα-2-naphthylsulfonylated 3-amidinophenylalanine type with a carboxylic group in the amide moiety as well as those derivatives in which the amidino function was replaced by another basic group showed improved pharmacological properties. In particular, a certain absorption has been found for the first time in benzamidine derivatives after oral application (PCT/CH 9100235).

This class of substances was then further developed. It has been found, for example, that by introducing new substituents at the N-4-atom of N-α-sulfonylated 3-amidinophenylalanine piperazides, in particular by introducing acyl- (—CO—X), sulfonyl (—SO₂—Y), carbamoyl-(—CO—NR'R") or functionalized alkyl residues, wherein X, Y and R',R" in the favorable case represent methyl groups and the functionalized alkyl residue ($C_1$–$C_3$) carries an OH group, the inhibitory efficacy against thrombin could be significantly improved and an extraordinary increase of the resorption capability could be surprisingly noted. This was observed in particular after rectal and intraduodenal application of the derivatives which were used either as salts or as free bases.

Not only the racemic mixtures, but also the pure optical antipodes were represented. Nα-(2-Naphthylsulfonyl)-3-amidino-(L)-phenylalanine-4-acetylpiperazide for example was synthesized within this framework. It has been found that this compound is not only a potent thrombin inhibitor and efficiently influences the coagulation, but that it surprisingly possesses improved pharmacokinetic properties. It is absorbed by the intestine in particular after rectal administration to rats and is present in the blood for a relatively long time period in a blood coagulation-inhibiting and antithrombotically efficient concentration. This also applies to compounds with other N-terminal protective groups which carry an N-substituted piperazine as the amide residue.

Besides effective and biologically available thrombin inhibitors, trypsin inhibitors which were highly effective in case of reduction in thrombin activity and which were also extensively absorbed after rectal application, were found in the presented class of substances among derivatives carrying at the piperazide nitrogen e.g. a heteroaryl or an acyl residue (—CO—X), wherein X represents a straight or branched alkyl ($C_3$–$C_{10}$), an aralkyl or a cycloalkyl residue ($C_3$–$C_{10}$). The inhibition of trypsin activity by inhibitors in hyperproteolytic states in the pancreas is of high therapeutic interest.

The present invention relates to new proteinase-inhibiting phenylalanine piperazides of the general formula I

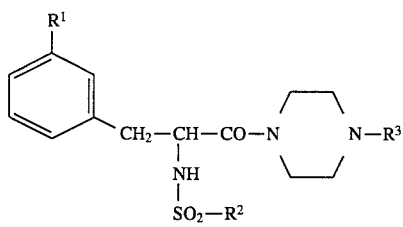

which can be present as racemates or as L- or D-configurated compounds and wherein $R^1$ represents a basic group of formula

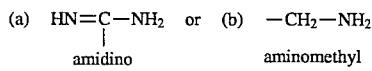

$R^2$ represents an (un)substituted aryl or heteroaryl residue e.g. phenyl, 4-methylphenyl, 2,4,6-trimethyl- or -triisopropylphenyl, 4-methoxy-2,3,6-trimethylphenyl, 2,2-dimethyl-6-methoxy- or 2,2,5,7,8-pentamethylchromanyl, anthraquinonyl, 1- or 2-naphthyl, quinolyl- or isoquinolyl or a camphor residue, and $R^3$ represents an acyl residue of formula —COX wherein X means H, unbranched or branched, possibly substituted alkyl, preferentially low alkyl, in particular methyl, (un)substituted aryl or cycloalkyl, preferentially $C_3$–$C_{10}$, an aralkyl residue in which the aromatic residue may be substituted with e.g. a halogen atom, an alkyl, alkoxy, hydroxy or nitro group, a carboxamide residue of formula —CONR'R", a thiocarboxamide residue of formula —CSNR'R" or an ethylamide residue of formula —CH₂—CONR'R" in which R'=R"=H; R'=R"=alkyl; R'=H, R"=alkyl; R'=H, R"=aryl, or R' and R" may form a cycloaliphatic or heterocycloaliphatic ring with the nitrogen atom, an SO₂—Y residue in which Y means (un)substituted alkyl, preferentially methyl, trifluoromethyl, trichloromethyl, (un)substituted aryl or heteroaryl, e.g. phenyl, 4-methylphenyl, 2,4,6-trimethyl- or -triisopropylphenyl, 4-methoxy-2,3,6-trimethylphenyl, 2,2-dimethyl-6-methoxy- or 2,2,5,7,8-pentamethylchromanyl, anthraquinonyl, naphthyl or quinolyl or O-aryl, preferentially phenyl, or -NR'R", in which R'and R"=H may be equal or not to low alkyl $C_1$–$C_3$, a cycloaliphatic ring with 5 to 8 C atoms which may be substituted with a hydroxyl or oxo group, an (un)substituted heteroaryl residue, e.g. pyridyl or pyrimidyl, or a heterocycloaliphatic residue, e.g. N-methylpiperidyl, a functionalized alkyl residue of formula —(CH₂)ₙ—X wherein the alkyl chain may be unbranched or branched, n=1 to 8 and the functional residue X represents a hydroxyl group the H atom of which can be substituted with an alkyl, aralkyl, aryl, hydroxyalkyl or acyl group, a halogen atom, a tertiary amino group of formula —N(Alk)₂ wherein the alkyl groups have 1 to 3 C atoms and the same denotation and, moreover, the nitrogen atom may belong to a cycloaliphatic ring with 5 to 7 ring parts to which one or two further rings may be added, an acylaminomalonate group of formula

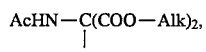

an

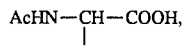

group, wherein Ac generally means formyl or acetyl and Alk=low alkyl or a

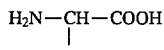

group, and the salts thereof with mineral or organic acids.

Among the phenylalanine piperazides defined in the general claims, the compounds wherein $R^1$ represents a basic group of formula (a)=amidino, $R^2$ represents a β-naphthyl, anthraquinone, 2,4,6-triisopropylphenyl and 2,2,5,7,8-pentamethylchroman group, and $R^3$ represents an acyl residue, in particular formyl and acetyl, a functionalized alkyl residue, e.g. 2-hydroxyethyl, an SO₂—Y residue, a carboxamide residue as well as heteroaryl residues such as 2-pyridyl or 2-pyrimidyl, are of particular importance.

Compounds of general formula I wherein $R^1$=amidino (a) are synthesized according to the known methods described hereinafter.

(D,L)-3-Cyanophenylalanine alkylesters of general formula II are converted in an adequate solvent with a sulfochloride of general formula III, wherein $R^2$ has the denotations described in general formula I, into the racemic compounds of general formula IV, from which racemates of the sulfonylated cyanophenylalanines V are obtained by acidic or alkaline hydrolysis.

The L-configurated sulfonylated amino acids V can be obtained by enzymatic ester hydrolysis of the compounds IV with chymotrypsin in an acetonitrile/water mixture. The D-configurated, sulfonylated amino alkyl carboxylates IV obtained by this procedure are converted into D-configurated sulfonylated amino carboxylic acids V by acidic hydrolysis in a mixture of 1N HCl and acetic acid by heating under reflux.

The cyano compounds with piperazide structure VI, which may have a racemic, or L or D configuration, respectively, can be obtained according to the usual coupling procedures from the correspondingly configurated compounds V with a piperazine derivative of general formula VII.

Moreover, the piperazides VI can be obtained by a principally known method consisting in first protecting racemic, L- or D-3-cyanophenylalanine by the introduction of a Boc group at the amino function. The obtained carboxylic acid V, with Boc group instead of $SO_2$—$R^2$, is transformed by conversion with a piperazine derivative VII, in a corresponding Boc-protected compound VI from which the cyano compounds with piperazide structure VI are obtained after acidic cleavage of the Boc group and conversion with a sulfochloride of general formula III.

Addition of $H_2S$ to the cyano function gives the thioamides VIII which are converted into the thioimidate halides IX by conversion with an alkyl halide. Moreover, the imidate halides X can be obtained from the cyano compounds VI in a known way.

To represent the target compounds of general formula I wherein $R^1$=amidino (a), having a racemic, or L or D configuration, respectively, and wherein $R^2$ and $R^3$ have the denotations mentioned in the general formula I and X=halogen, preferentially chlorine, the thioimidate salts IX are converted into compounds of general formula I in an alcoholic solution with ammonium acetate or the imidate salts X are converted into compounds of general formula I in an alcoholic ammonia solution. The amidine salts thereby obtained can be converted in an adequate way into free bases.

The compounds of general formula I wherein $R^1$=aminomethyl (b) are obtained from the cyano compounds VI by catalytic hydrogenation, e.g. Raney-Nickel/hydrogen in adequate solvents in the presence of ammonia.

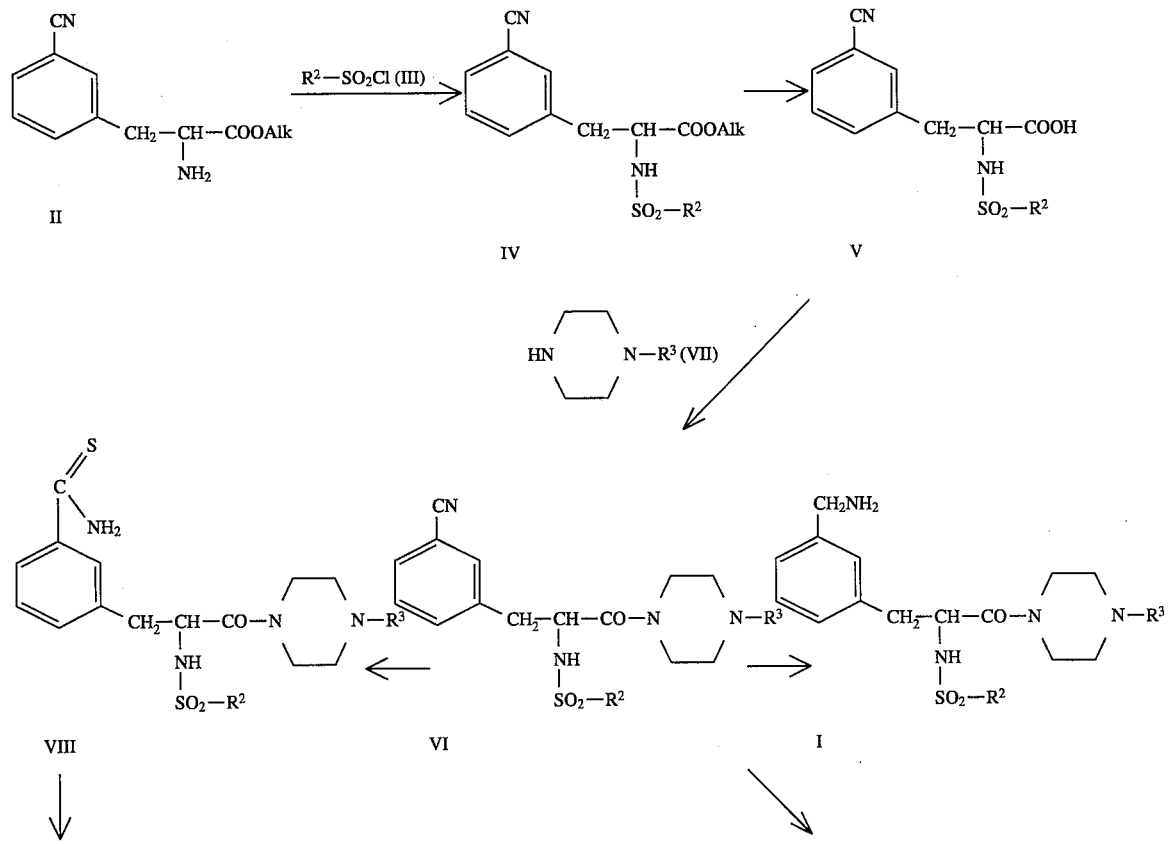

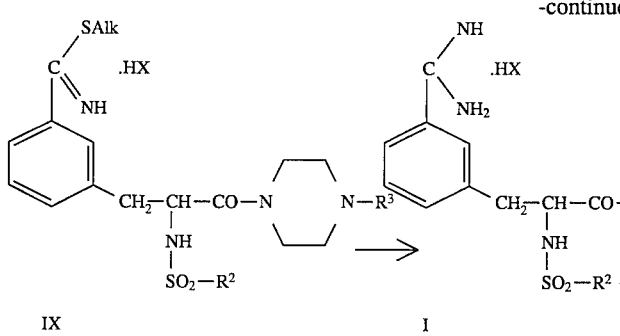 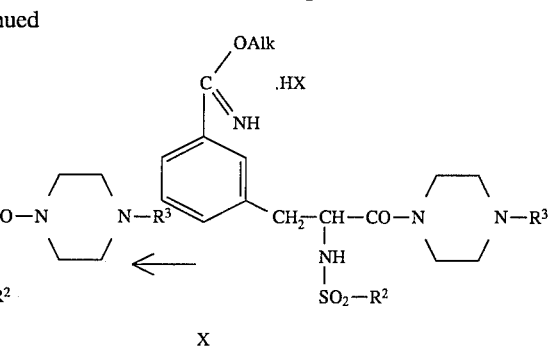

The biological activity of the compounds of the present invention was determined in vitro as well as in vivo. For characterizing the inhibitory activity in vitro, the dissociation constants $K_i$ for the inhibition of thrombin and the related enzymes trypsin, plasmin, factor $X_a$, factor $XII_a$, plasma kallikrein, glandular kallikrein and tPA, respectively, were calculated according to the formula $$K_i = \frac{[E] \cdot [I]}{[EI]}$$

wherein [E] represents the concentration in free enzyme, [I] the concentration in free inhibitor and [EI] the concentration in enzyme-inhibitor complex (Dixon, Biochem. J. 55, 170–173 [1953]). The smaller the $K_i$-value for a tested enzyme, the higher the affinity of the inhibitor for the enzyme and the smaller the quantity of inhibitor needed for the inhibition of the enzyme, e.g. thrombin.

Various coagulation tests were used in vitro to determine the efficacy of the inhibitors towards the thrombin-induced coagulation of its natural substrate fibrinogen. For that purpose, the thrombin time (TT), the activated partial thromboplastin time (aPTT) and the prothrombin time (PT, Quick value) were determined in human plasma.

The toxicity of the compounds of the present invention was evaluated by determination of the $LD_{50}$ (=dose that causes the death of 50% of the test animals within an observation time of one week) in the mouse after intravenous and peroral administration, respectively.

For the pharmacokinetic characterization, the plasma concentration of selected derivatives was determined in rats after intravenous (i.v.), peroral (p.o.), intraduodenal (i.d.) and rectal application according to the following three-step procedure:

1. A physiological NaCl solution of the substance to be tested was submitted to high pressure liquid chromatography (HPLC) in order to determine its characteristic substance-specific retention time with the chosen test conditions.
2. The substance to be tested was diluted in vitro in rat plasma. This solution was also submitted to HPLC to see whether the characteristic peak of the substance once again appeared at the substance-specific retention time.
3. The substance to be tested was dissolved in physiological NaCl solution and administered i.v., p.o., i.d. and rectally, respectively, to rats in doses of 1, 50 and 100 mg per kg body weight. Blood samples were taken at time intervals of 15 minutes, from which plasma samples were prepared by centrifugation; those samples were also submitted to HPLC to see whether the characteristic peak of the substance appeared again at the substance-specific retention time.

To demonstrate the pharmacological efficacy, the substance to be tested was dissolved in physiological NaCl solution and administered rectally to rats in doses of 5 and 20 mg per kg body weight, respectively. Blood samples were taken at time intervals, from which plasma samples were prepared by centrifugation and investigated in the coagulation test (thrombin time TT and activated partial thromboplastin time aPTT).

The antithrombotic activity of the compounds was determined in the rat on the model of the stasis-induced thrombosis according to Wessler et al. (J. Appl. Physiol. 14, 943–946, 1959). The thrombus was induced by serum 30 min after application of the inhibitor and macroscopically evaluated after 10 further min.

The compounds of the present invention can be used as diagnostics or drugs in adequate application forms either as their salts or free bases.

The invention is explained in detail in the four examples described hereafter.

EXAMPLE 1

Nα-(2-naphthylsulfonyl)-3-amidino-(L)-phenylalanine-4-acetyl-piperazide

Nα-(2-naphthylsulfonyl)-3-cyano-(D,L)-phenylalaninemethyl-ester (formula IV; Alk=—$CH_3$, $R^2$=β-naphthyl)

24.1 g (0.1 mol) of 3-cyano-(D,L)-phenylalaninemethyl-ester hydrochloride was suspended in 200 ml of dioxane, 20.6 g (0.204 mol) of N-methylmorpholine was added under stirring and a solution of 23.6 g (0.104 mol) of 2-naphthylsulfonylchloride in 200 ml of ethyl acetate was added dropwise. The mixture was stirred for 16 hours at room temperature, the precipitated N-methylmorpholine hydrochloride was filtered off and the solvent evaporated under reduced pressure. The residue was dissolved in 50 ml of methanol, 50 ml of diethylether was added and the mixture was allowed to crystallize. The formed precipitate was filtered off, washed with diethylether and dried in a vacuum desiccator ($KOH/H_2SO_4$). Yield: 36 g (91.3%). Mp: 122°–123° C. TLC: $R_f$=0.65 (chloroform 40/methanol 4/acetic acid 1//v/v/v/)

Nα-(2-naphthylsulfonyl)-3-cyano-(L)-phenylalanine (formula V; $R^2$ =β-naphthyl)

17.4 g (0.044 mol) of Nα-(2-naphthylsulfonyl)-3-cyano-(D,L)phenylalanine methylester was dissolved in 260 ml of acetonitrile, 130 ml of water, 100 mg of chymotrypsin as well as 0.785 g of potassium chloride was added and the pH of the solution was adjusted to 6.8–7 with 2 N NaOH. After stirring for 24 hours at room temperature, another 50 mg of chymotrypsin were added to the mixture after 5 and again after 10 hours and the above mentioned pH of the solution was maintained by controlled addition of a total of 11 ml of 2 N NaOH. After subsequent filtration, the acetonitrile was evaporated under reduced pressure and the aqueous solution was extracted several times with ethyl acetate. After acidification with 1 N HCl the aqueous phase was again extracted with ethyl acetate, the collected organic phases were washed with saturated sodium chloride solution, dried over magnesium sulfate, and the solvent was evaporated under reduced pressure, whereupon the product began to crystallize towards the end of the distillation. After interruption of the distillation, 30 ml of diethylether and 70 ml of hexane was added, the precipitate was filtered off, washed with a small amount of diethylether and dried. Yield: 7.2 g (85.8%). Mp: 192°–193° C. $[\alpha]_D^{20}$=+11.9° (C=3, in methanol) TLC: $R_f$=0.25 (chloroform 40/methanol 4/acetic acid 1//v/v/v) Nα-(2-naphthylsulfonyl)-3-cyano-(L)-phenylalanine-4-acetylpiperazide (formula VI; $R^2$=β-naphthyl, $R^3$=—COCH$_3$)

1.59 g (13.2 mmol) of 1-acetylpiperazine was dissolved in 10 ml of THF and 20 ml of DMF; the solution was mixed with 1.28 g (7.9 mmol) of HOBt and 2.5 g (6.6 mmol) of Nα-(2-naphthyl-sulfonyl) -3-cyano-(L)-phenylalanine and cooled to 0° C. After addition of 1.5 g (7.3 mmol) of DCC, the solution was stirred for 2 hours at 0° C. and then for 22 hours at room temperature. The precipitated dicyclohexyl urea was filtered off and the solvent evaporated under reduced pressure. The residue was dissolved in chloroform and purified by column chromatography over silica gel 60 with chloroform/methanol 93:7 as the eluent. 2.9 g (90%) of an amorphous product were obtained.

$[\alpha]_D^{20}$ =+46.3° (C=1, in methanol) TLC: $R_f$=0.36 (chloroform 40/methanol 4/acetic acid 1//v/v/v)
Nα-(2-naphthylsulfonyl)-3-thiocarboxamido-(L)-phenylalanine 4-acetylpiperazide (formula VIII; $R^2$=β-naphthyl, $R^3$=—COCH$_3$)

2.75 g (5.6 mmol) of Nα-(2-naphthylsulfonyl)-3-cyano-(L)-phenylalanine-4-acetylpiperazide was dissolved in 25 ml of pyridine. Twenty drops of TEA were added to the solution which was saturated by introducing H$_2$S for 10 min. The reaction mixture was allowed to stand at room temperature for 2 days, whereupon the solvent was evaporated and the residue was dissolved in ethyl acetate and extracted with 1 N HCl The organic phase was washed with saturated sodium chloride solution, dried over magnesium sulfate and the solvent was evaporated. 2.6 g (88%) of yellow, amorphous product were obtained and further processed in this form.
Nα-(2-naphthylsulfonyl)-3-S-methyliminothiocarbonyl-(L)- phenylalanine-4-acetylpiperazide hydroiodide (formula IX; Alk=—CH$_3$, X=I, $R^2$=β-naphthyl, $R^3$=—COCH$_3$)

2.6 g (4.96 mmol) of the previously described thioamide was dissolved in 60 ml of acetone, 6 g (42.3 mmol) of methyliodide was added to the solution and the reaction mixture was allowed to stand in the dark for 20 hours at room temperature. Afterwards, the solvent was evaporated, the oily residue was triturated with isopropanol/diethylether, the obtained powder was filtered off, washed with diethylether and dried. Yield: 3.1 g (94%).
Nα-(2-naphthylsulfonyl)-3-amidino-(L)-phenylalanine-4-acetylpiperazide hydrochloride (formula I; X=Cl, $R^2$=β-naphthyl, $R^3$=—COCH$_3$)

3.0 g (4.5 mmol) of methyl-thioimidate hydroiodide was dissolved in 100 ml of methanol, 0.8 g (10.4 mmol) of ammonium acetate was added to the solution and the test mixture was heated for 3 hours at 60° C. in a water bath. The solvent was then evaporated, the residue was dissolved in warm isopropanol and the amidine hydroiodide was precipitated with ethyl acetate, filtered off, washed with ethyl acetate and diethylether and dried. For the conversion into the hydrochloride, the obtained product was dissolved in methanol and the solution passed over a strongly basic ion exchanger (Amberlite IRA-410, loaded with Cl$^-$). The hydrochloride was precipitated from the concentrated methanolic solution with ethyl acetate/diethylether 1:1. Yield: 1.8 g (73.5%). $[\alpha]_D^{20}$=+61.8° (C=1 in methanol) TLC: $R_f$=0.2 (organic phase of ethyl acetate 4/acetic acid water 2//v/v/v) Specific rotation of the corresponding (D)-configurated compound: $[\alpha]_D^{20}$=−62.2° (C=1, in methanol)

EXAMPLE 2

Nα-(2-naphthylsulfonyl)-3-amidino-(L)-phenylalanine-4-(2hydroxyethyl)-piperazide Nα-(2-naphthylsulfonyl)-3-cyano-(L)-phenylalanine-4-(2hydroxyethyl) -piperazide hydrochloride (formula VI; $R^2$=β-naphthyl, $R^3$=—CH$_2$CH$_2$OH)

2.0 g of Nα-(2-naphthylsulfonyl)-3-cyano-(L)-phenylalanine was added to 10 ml of thionyl chloride and the mixture was heated for 30 min. under reflux. After cooling, the obtained solution was treated with hexane until a turbid solution was obtained. The crystallized acid chloride was filtered off after 1 hour, washed with hexane and vacuum-dried. 1.7 g (4.26 mmol) of this product was dissolved in 25 ml of THF and added dropwise within 15 min. under stirring to a solution of 1.16 g (8.9 mmol) of 1-(2-hydroxyethyl)-piperazine in 15 ml of THF. After 1 hour of stirring, the precipitated 1-(2-hydroxyethyl)-piperazine hydrochloride was filtered off and the solvent evaporated. The remaining residue was dissolved in 15 ml of methanol, water was added until a turbid solution was obtained, the mixture was allowed to stand overnight, whereby the piperazide separated itself as an oil. After removal of the supernatant, the oil was taken up in 100 ml of ethyl acetate, the ethyl acetate solution was washed with saturated sodium chloride solution, dried over MgSO$_4$ and concentrated under vacuum. The resulting solution was acidified with 2 N ethyl acetate/HCl whereupon 50 ml of diethylether were added. The formed precipitate was filtered off after 1 hour of standing, washed with diethylether and vacuum-dried. Yield: 1.65 g (73%). $[\alpha]_D^{20}$=−5.4° (C=1, in methanol) TLC: $R_f$=0.43 (organic phase of ethyl acetate 4/acetic acid 1/water 2//v/v/v)

Nα-(2-naphthylsulfonyl)-3-methoxyiminocarbonyl-(L)-phenylalanine-4-(2-hydroxyethyl)-piperazide dihydrochloride (formula X; Alk=—CH$_3$, X=Cl, $R^2$=β-naphthyl, $R^3$=—CH$_2$CH$_2$OH)

1.4 g (2.65 mmol) of the previously described cyano compound was dissolved in a mixture of 7.5 ml of abs. methanol and 10 ml of abs. dioxane, 5.2 g (0.143 mol) of dried HCl gas was introduced into the solution under ice cooling and the mixture was kept for 3 days in the refrigerator. Afterwards, the mixture was poured into 150 ml of diethylether, the formed precipitate was worked up after removal of the supernatant, suspended in 40 ml of abs. ethanol, the crystalline powder filtered off, washed with ethanol, diethylether and dried. Yield : 1.44 g (91%). TLC: $R_f$=0.15 (organic phase of ethyl acetate 4/acetic acid 1/water 2//v/v /v) TLC: $R_f$=0.95 (chloroform 70 /methanol 42/acetic acid 0.5/ water 10//v/v/v)
Nα-(2-naphthylsulfonyl)-3-amidino-(L)-phenylalanine-4-(2-hydroxyethyl) -piperazide dihydrochloride (formula I; X=Cl, $R^2$=β-naphthyl, $R^3$=—CH$_2$CH$_2$OH)

1.3 g (2.18 mmol) of the previously described methylimidate dihydrochloride was suspended in 30 ml of methanol and ethanolic ammonia solution was added under stirring until a pH of 8.7 was reached, whereby a clear solution was obtained. The mixture was heated for 3 hours at 60° C. in a water bath, the solvent was then evaporated under reduced pressure, the residue was dissolved in 15 ml of abs. ethanol and, after addition of 20 drops of 2N ethyl acetate/HCl, the amidine dihydrochloride was precipitated with ethyl acetate, filtered off, washed with ethyl acetate and diethylether and dried. Yield: 1.02 g (80.3%). $[\alpha]_D^{20}=+14.2°$ (C=1, in methanol) TLC: $R_f=0.18$ (organic phase of ethyl acetate 4/acetic acid 1/water 2//v/v/v) TLC: $R_f=0.6$ (chloroform 70/methanol 42/acetic acid 0.5/ water 10//v/v/v)

Specific rotation of the corresponding (D)-configurated compound: $[\alpha]_D^{20}=15.0°$ (C=1, in methanol)

To obtain the free base, 0.5826 g (1 mmol) of amidine dihydrochloride was dissolved in 20 ml of methanol, the equimolar quantity of 0.1N NaOH (20.00 ml) was added to the solution and the solvent was evaporated under reduced pressure. To remove the still present water traces, a co-distillation with toluene/isopropanol was performed several times. The base obtained in this way still contains NaCl. To eliminate the inorganic component, a mixture of 15 ml of abs. ethanol, 10 ml of chloroform and 10 ml of diethylether was added, whereby after stirring, the base dissolved. Insoluble NaCl was filtered off and the solvent evaporated under reduced pressure. The remaining residue solidified when triturated with diethylether. Yield: 0.48 g (94%)

EXAMPLE 3

Nα-(2-naphthylsulfonyl)-3-amidino-(L)-phenylalanine-4-methylsulfonylpiperazide

Nα-(2-naphthylsulfonyl)-3cyano-(L)-phenylalanine-4-methylsulfonylpiperazide (formula VI, $R^2$=β-naphthyl, $R^3$=—$SO_2CH_3$)

1.56 g (7.8 mmol) of 1-methylsulfonylpiperazine.HCl was suspended in 15 ml of DMF, the suspension was mixed under stirring with 0.86 ml (7.8 mmol) of NMM, 1.16 g (7.8 mmol) of HOBt, 2.7 g of Nα-(2-naphthylsulfonyl)-3-cyano-(L)-phenylalanine (7.1 mmol) and 70 ml of THF and cooled to 0° C. After addition of 1.61 g of DCC (7.8 mmol), the mixture was stirred for another 20 hours at room temperature. Afterwards, the precipitated dicyclohexyl urea was filtered off and the solvent evaporated under reduced pressure. The residue was dissolved in chloroform and purified by column chromatography over silica gel 60 with chloroform as the eluent. 3.34 g (89%) of an amorphous product were obtained.

$[\alpha]_D^{20}=+47.3°$ (C=1, in methanol) TLC: $R_f=0.36$ (chloroform 40/methanol 4/acetic acid 1//v/v/v)

Nα-(2-naphthylsulfonyl)-3-thiocarboxamido-(L)-phenylalanine-4-methylsulfonylpiperazide (formula VIII; $R^2$=β-naphthyl, $R^3$=$SO_2CH_3$)

2.9 g (5.2 mmol) of the previously described cyano compound was dissolved in 35 ml of pyridine, 15 drops of TEA was added and the solution was saturated by 10-min. introduction of $H_2S$. The mixture was allowed to stand at room temperature for 2 days. The solvent was then evaporated under reduced pressure and the residue dissolved in ethyl acetate, whereby the thioamide progressively crystallized out. The precipitate was filtered off, washed with ethyl acetate and dried. Yield: 2.98 g (96%).

Nα-(2-naphthylsulfonyl)-3-S-methyliminothiocarbonyl-(L)-phenylalanine-4-methylsulfonylpiperazide (formula IX; Alk =$CH_3$, X=I, $R^2$=β-naphthyl, $R^3$=—$SO_2CH_3$)

2.95 g (5.26 mmol) of the described thioamide was dissolved in 4 ml of DMF under heating, to the solution 50 ml of acetone and 7.1 g (50 mmol) of methyliodide was added and the mixture was kept in the dark for 20 hours at room temperature. After pouring in 400 ml of diethylether, the formed precipitate was filtered off, washed with diethylether and dried. Yield: 3.25 g (88%).

Nα-(2-naphthylsulfonyl)-3-amidino-(L)-phenylalanine-4methylsulfonylpiperazide hydrochloride (formula I; X=Cl, $R^2$=β-naphthyl, $R^3$=—$SO_2CH_3$)

3.23 g (4.6 mmol) of methyl-thioimidate hydroiodide was dissolved in 110 ml of methanol, 0.58 g (7.5 mmol) of ammonium acetate was added to the solution and the mixture was heated for 3 hours at 60° C. in a water bath. Afterwards, the solvent was evaporated under reduced pressure, the residue dissolved in methanol and the amidine hydroiodide precipitated with ethyl acetate/diethylether 9:1, filtered off, washed with diethylether and dried. For the conversion into the hydrochloride, the obtained product was dissolved in methanol and the solution passed over a strongly basic ion exchanger (Amberlite IRA-410, loaded with Cl⁻). The hydrochloride was precipitated from the concentrated methanolic solution with diethylether.

Yield: 2.1 g (79%). $[\alpha]_D^{20}=+70.0°$ (C=1, in methanol). TLC: $R_f=0.32$ (organic phase of ethyl acetate 4/acetic acid 1/water 2//v/v/v) Specific rotation of the corresponding (D)-configurated compound: $[]D^{20}=-70.5°$ (C=1, in methanol)

EXAMPLE 4

Pmc-3-amidino-(L)-phenylalanine-4-methylsulfonyl-piperazide

Boc-3-cyano-(L)-phenylalanine 6 g (26.5 mmol) of 3-cyano-(L)-phenylalanine hydrochloride and 9.1 ml (53.2 mmol) of N-ethyldiisopropylamine was suspended in 17 ml of water. To this suspension was added a solution of 7.2 g (29.2 mmol) of 2-(Boc-oxyimino)-2-phenylacetonitrile in 20 ml of dioxane and stirring continued for 16 hours at room temperature. After subsequent addition of 50 ml of water, the solution was extracted with 50 ml of ethyl acetate, the organic phase separated and the pH of the aqueous phase adjusted to 3 with dilute hydrochloric acid. After 3 extractions with 100 ml each of ethyl acetate, the collected organic solutions were washed with saturated sodium chloride solution, dried over magnesium sulfate and the solvent was evaporated under reduced pressure.

Yield: 6.2 g (81%)

Boc-3-cyano-(L)-phenylalanine-4-methylsulfonylpiperazide 4.92 g (24.5 mmol) of 1-methylsulfonylpiperazine hydrochloride and 2.7 ml (24.5 mmol) of NMM was dissolved in 50 ml of DMF. After addition of 4 g (29.6 mmol) of HOBt and a solution of 5.93 g (20.4 mmol) of Boc-3-cyano-(L)-phenylalanine in 200 ml of THF, the mixture was cooled to 0° C. 5.1 g (24.7 mmol) of DCC were added and the mixture was stirred for 48 hours at room temperature. Afterwards, the precipitated dicyclohexyl urea was filtered off, the THF moiety of the solution evaporated under reduced pressure, filtered and the filtrate poured into a mixture of 100 ml of 5% sodium bicarbonate solution and 200 ml of ice water. The formed precipitate was filtered off, washed with water, dissolved in methanol and the solvent was evaporated under reduced pressure. To remove the still present water, a co-distillation with toluene/isopropanol was performed several times. The only slightly impure product was processed in this form. Yield: 7.9 g (89%)

3-Cyano-(L)-phenylalanine-4-methylsulfonylpiperazide hydrochloride 7.9 g of the previously described crude product was dissolved in 70 ml of ethyl acetate and 30 ml of diethylether, 50 ml of 2.5 N HCl in ethyl acetate was added and the solution was stirred for 48 hours at room temperature, whereby the desired hydrochloride crystallized out. After addition of 200 ml of diethylether, the mixture was stirred for 1 hour, the precipitate filtered off, washed with diethylether and dried.

Yield: 4.95 g (73%)

Pmc-3-cyano-(L)-phenylalanine-4-methylsulfonyl piperazide (formula VI; $R^2$=—Pmc, $R^3$=—$SO_2CH_3$)

4.76 g (12.8 mmol) of 3-cyano-(L)-phenylalanine-4-methylsulfonyl piperazide hydrochloride and 1.29 g (12.8 mmol) of NMM was dissolved in 25 ml of DMF, 4.64 g (15.3 mmol) of Pmc-chloride and 1.55 g (15.3 mmol) of NMM was added and the mixture was stirred for 48 hours at room temperature. Precipitated NMM hydrochloride was then filtered off and the solvent evaporated under reduced pressure. The residue was taken up in ethyl acetate and the organic phase washed with 0.1 N HCl and saturated sodium chloride solution. After drying over magnesium sulfate, the solvent was evaporated under reduced pressure. The obtained product was purified by column chromatography over silica gel 60 with chloroform as the eluent.

Yield: 6.45 g (84%).

$[\alpha]_D^{20}$=+10.4° (C=1, methanol) TLC: $R_f$=0.66 (chloroform 40/ methanol 4/acetic acid 1//v/v/v)

Pmc-3-thiocarboxamido-(L)-phenylalanine-4-methylsulfonyl piperazide (formula VII;
$R^2$=—Pmc, $R^3$=—$SO_2CH_3$)

6.34 g (0.5 mmol) of the previously described cyano compound was dissolved in 40 ml of pyridine, 20 drops of TEA were added and the solution was saturated by introduction of $H_2S$ for 10 minutes. The reaction mixture was kept at room temperature for 2 days. The solvent was then evaporated under reduced pressure; the solid residue was suspended in 100 ml of ethyl acetate, briefly heated, filtered off, washed with ethyl acetate and dried.

Yield: 5.86 g (88%).

Pmc-3-S-methyliminothiocarbonyl-(L)-phenylalanine-4-methylsulfonyl piperazide (formula IX; Alk=—$CH_3$, X=I, $R^2$=—Pmc, $R^3$=—$SO_2CH_3$)

5.86 g (7.52 mmol) of the previously described thioamide was dissolved under heating in 11 ml of DMF, 250 ml of acetone and 13 g (92 mmol) of methyl iodide was added and the mixture was kept in the dark overnight at room temperature. The mixture was then poured into 1 l of diethylether and stirred for 1 hour, whereupon the formed precipitate was filtered off, washed with diethylether and dried.

Yield: 6.23 g (87%).

Pmc-3-amidino-(L)-phenylalanine-4-methylsulfonyl piperazide hydrochloride (formula I; X=Cl, $R^2$=—Pmc, $R^3$=—$SO_2CH_3$)

6.23 g (8 mmol) of thioimidate hydroiodide was dissolved in 350 ml of abs. methanol. After addition of 1 g (13 mmol) of ammonium acetate, the mixture was heated to 60° C. in a water bath under stirring, whereby a precipitate formed which needed 4 hours to completely dissolve again. The reaction was followed by thin layer chromatography (TLC) and a total of 1 g (13 mmol) of ammonium acetate in portions of 0.2, 0.5 and 0.3 g was added after 2, 4 and 6 hours, respectively. After 8 hours, no initial compound could be detected anymore by TLC. The solvent was then evaporated under reduced pressure, the residue dissolved in ethanol and the amidine hydroiodide precipitated with ethyl acetate/ diethylether 1:1. For the conversion into the hydrochloride, the obtained product was dissolved in methanol and the solution passed over a strongly basic ion exchanger (Amberlite IRA-410, loaded with $Cl^{31}$). The hydrochloride was precipitated from the concentrated methanolic solution with diethylether.

Yield: 3.34 g (64%). $[\alpha]_D^{20}$=+47.7° (C=1, in methanol). TLC: $R_f$=0.5 (organic phase of ethyl acetate 4/acetic acid 1/water 2//v/v/v) Specific rotation of the corresponding (D)-configurated compound: $[\alpha]_D^{20}$=−48.3° (C=1, in methanol)

All the amidine hydrochlorides were purified by column chromatography over Sephadex LH-20 with methanol as the eluent.

| Abbreviations | |
|---|---|
| Ac | acetyl |
| AcONHiPr | —$CH_2CONHCH(CH_3)_2$ |
| BOC | t-butyloxycarbonyl |
| Bzl | benzyl |
| cBu | cyclobutyl |
| cHex | cyclohexyl |
| cPr | cyclopropyl |
| DCC | dicyclohexylcarbodiimide |
| DMF | dimethylformamide |
| Et | ethyl |
| EtOH | hydroxyethyl |
| EtOEtOH | hydroxyethyl-ethoxy |
| For | formyl |
| HOBt | hydroxybenzotriazole |
| Me | methyl |
| NMM | N-methylmorpholine |
| Ph | phenyl |
| TEA | triethylamine |
| THF | tetrahydrofuran |

LEGENDS TO THE TABLES 1–2

| $R_1$ | $R_2$ |
|---|---|
| AMD = amidino | Mtr = 2,3,6-methyl-4-methoxy-phenyl |
| AMe = aminomethyl | TIPP = 2,4,6-triisopropyl-phenyl |
| | TMeP = 2,4,6-trimethyl-phenyl |
| | Tol = 4-methyl-phenyl |
| | 2-Naph = β-naphthyl |
| | 1-Naph = α-naphthyl |

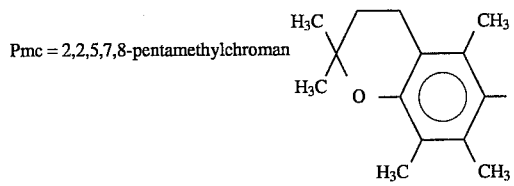

Pmc = 2,2,5,7,8-pentamethylchroman

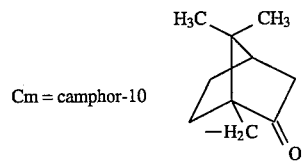

Cm = camphor-10

LEGENDS TO THE TABLES 1–2

| R₁ | R₂ |
|---|---|
| AC = anthraquinone | (anthraquinone structure) |
| R₃ | |
| 2-Pyl = 2-pyridyl | (2-pyridyl structure) |
| 2-Pym = 2-pyrimidyl | (2-pyrimidyl structure) |

The biological properties of some representative compounds of the present invention are mentioned hereafter:

Table 1 shows the inhibition of the clotting enzyme thrombin as compared to trypsin by the cited compounds by means of the dissociation constant $K_i$ (expressed in μmol/l). All the compounds investigated competitively inhibit the substrate splitting caused by the two enzymes. Among the derivatives of 3-amidinophenylalanine listed in Table 1, there is a series of compounds having a high antithrombin activity, i.e. with $K_i$-values between 0.1 and 0.001 μmol/l. In most compounds, the thrombin inhibition is more pronounced than the inhibition of trypsin. The $K_i$-values for the inhibition of trypsin are higher by up to one order of magnitude than those for thrombin inhibition. A series of compounds inhibit thrombin and trypsin with a comparable affinity, while derivatives, in particular those with defined acyl or heteroaryl residues at the piperazin nitrogen, are potent trypsin inhibitors.

Table 1 also shows the inhibitory activity towards plasmin, factor $X_a$, factor $XII_a$, plasma kallikrein, glandular kallikrein and tPA. The inhibition of plasmin, factor $X_a$ and plasma kallikrein is usually much weaker, the $K_i$-values are higher by 1–2 orders of magnitude. The derivatives are practically ineffective towards factor $XII_a$, tPA and glandular kallikrein. Therefore, some compounds are said to be selective thrombin inhibitors, while other derivatives give preference to trypsin.

In a series of compounds of the present invention, the toxicity is comparable to that of the previously investigated derivatives of benzamidine-containing amino acids ($LD_{50}$ 10–50 mg/kg after i.v. application).

The optical antipodes of some derivatives were represented and their inhibitory effect was studied. According to the results of Turk, D. et al. (FEBS Letters 287, 133–138, 1991), the L-enantiomers were the most effective form; as compared to the isomer mixtures, their inhibitory effect was increased by a factor of 2. The inhibitory effect of the D-forms is lower by 2 orders of magnitude.

The 2-naphthylsulfonyl protective group can be replaced by an AC—$SO_2$, Pmc—$SO_2$, Mtr-$SO_2$, Cm-$SO_2$ or TIPP—$SO_2$ residue. Highly potent inhibitors are also found.

The compounds that are not characterized with (L) or (D) in Table 1 are racemates and NAPS-F(3AMD)-Pzd(N-COOEt) denotes N-α-(2-naphthylsulfonyl)-(D,L)-3-amidinophenylalanine-4-ethoxycarbonyl piperazide.

TABLE 1

Inhibition of various trypsin-like serine proteinases by substituted piperazides of Nα-protected 3-substituted phenylalanines

| R¹ | R² | R³ | Nr | Thrombin | Trypsin | Plasmin | Factor Xa | Factor XIIa | Plasma kallikr. | Gland. kallikr. | tPA |
|---|---|---|---|---|---|---|---|---|---|---|---|
| NAPAP | | | | 0.006 | 0.69 | 30 | 7.9 | 450 | 14 | 93 | 70 |
| NAPS-F(3AMD)-Pzd(N-COOEt) | | | X | 0.67 | 0.022 | 2.5 | 54 | 210 | 30 | >1000 | 370 |
| AMD | 2-Naph | For | | 0.037 | 0.22 | 6.3 | 19 | 83 | 16 | 440 | >1000 |
| AMD(L) | 2-Naph | For | | 0.011 | 0.073 | 3.3 | 9.7 | 42 | 3.6 | >1000 | 120 |
| AMD | 2-Naph | Ac | 1 | 0.023 | 0.14 | 8.4 | 48 | 210 | 28 | >1000 | >1000 |
| AMD(L) | 2-Naph | Ac | 2 | 0.012 | 0.044 | 5.4 | 35 | 150 | 15 | >1000 | 440 |
| AMD | 2-Naph | SO₂Me | | 0.0028 | 0.19 | 12 | 22 | 86 | 77 | >1000 | >1000 |
| AMD(L) | 2-Naph | SO₂Me | 5 | 0.0021 | 0.067 | 9.0 | 19 | 52 | 9.2 | >1000 | 190 |
| AMD | 2-Naph | SO₂Et | | 0.044 | 0.19 | 3.5 | 24 | 212 | 58 | >1000 | 820 |
| AMD | 2-Naph | SO₂-Ph | | 0.041 | 0.33 | 19 | 24 | 120 | 36 | >1000 | >1000 |
| AMD | 2-Naph | SO₂-Tol | | 0.022 | 0.22 | 15 | 24 | >1000 | 30 | >1000 | >1000 |
| AMD | 2-Naph | SO₂-2-Naph | | 0.024 | 0.40 | 11 | 25 | 90 | 22 | >1000 | >1000 |
| AMD | 2-Naph | SO₂-TMeP | | 0.075 | 0.59 | 31 | 13 | 690 | 1.0 | >1000 | >1000 |
| AMD | 2-Naph | SO₂-Mtr | | 0.05 | 1.5 | 37 | 25 | 7.6 | 6.9 | >1000 | >1000 |
| AMD | 2-Naph | CO-N(Me)₂ | | 0.0088 | 0.17 | 6.1 | 24 | 200 | 47 | >1000 | >1000 |
| AMD(L) | 2-Naph | CO-N(Me)₂ | 6 | 0.004 | 0.097 | 4.9 | 15 | 51 | 7.3 | >1000 | >1000 |
| AMD | 2-Naph | CO-N(Me)₂ | | 0.013 | 0.049 | 6.2 | 22 | 130 | 28 | >1000 | >1000 |
| AMD | 2-Naph | EtOH | | 0.058 | 1.1 | 42 | 35 | >1000 | 74 | >1000 | >1000 |
| AMD(L) | 2-Naph | EtOH | 3 | 0.036 | 0.60 | 21 | 22 | 320 | 25 | >1000 | 190 |
| AMD | 1-Naph | SO₂Me | 11 | 0.026 | 0.32 | 5.0 | 9.7 | >1000 | 79 | >1000 | >1000 |
| AMD | 1-Naph | CO₂N(Me)₂ | | 0.068 | 0.25 | 4.8 | 5.9 | 72 | 37 | >1000 | 270 |
| AMD | Pmc | Ac | | 0.074 | 0.60 | 11.5 | 150 | 420 | 44 | 760 | 670 |
| AMD | Pmc | SO₂Me | | 0.0074 | 0.76 | 30 | 75 | 140 | 140 | >1000 | >1000 |
| AMD(L) | Pmc | SO₂Me | 10 | 0.0053 | 0.32 | 10.3 | 37 | >1000 | 110 | >1000 | 600 |
| AMD | Pmc | CO-N(Me)₂ | | 0.033 | 0.58 | 13 | 26 | >1000 | 93 | >1000 | >1000 |
| AMD | Pmc | EtOH | | 0.059 | 3.3 | 48 | 91 | >1000 | 180 | >1000 | >1000 |
| AMD | Mtr | SO₂Me | | 0.032 | 1.8 | 18 | 120 | 630 | 150 | >1000 | >1000 |
| AMD(L) | Mtr | SO₂Me | 9 | 0.020 | 0.86 | 8.2 | 48 | >1000 | 170 | >1000 | 600 |
| AMD(L) | (−)Cm | SO₂Me | 7 | 0.012 | 0.22 | 14 | 1.1 | 61 | 25 | >1000 | 20 |
| AMD(L) | (+)Cm | SO₂Me | 8 | 0.031 | 0.44 | 29 | 6.7 | 70 | 130 | >1000 | 82 |

TABLE 1-continued

Inhibition of various trypsin-like serine proteinases by substituted piperazides of Nα-protected 3-substituted phenylalanines

| | | | | $K_i$, µmol/l | | | | | | | |
|---|---|---|---|---|---|---|---|---|---|---|---|
| $R^1$ | $R^2$ | $R^3$ | Nr | Thrombin | Trypsin | Plasmin | Factor Xa | Factor XIIa | Plasma kallikr. | Gland. kallikr. | tPA |
| AMD | TIPP | Ac | | 0.098 | 0.22 | 3.0 | 4.0 | 47 | 7.3 | 200 | 17 |
| AMD | AC | Ac | 4 | 0.014 | 0.026 | 8.6 | 4.1 | 52 | 7.0 | >1000 | >1000 |
| AMD | AC | For | | 0.031 | 0.033 | 13 | 1.7 | 7.2 | 11 | >1000 | 84 |
| AMD | 2-Naph | 2-Pyl | | 0.52 | 0.035 | 3.3 | 12 | 84 | 19 | >1000 | >1000 |
| AMD | 2-Naph | 2-Pym | | 1.8 | 0.061 | 3.3 | 14 | 100 | 19 | >1000 | 320 |
| AMD | 2-Naph | COCH(Me)$_2$ | | 0.26 | 0.063 | 9.3 | 84 | >1000 | 50 | >1000 | 440 |
| AMD | 2-Naph | COCH$_2$OMe | | 1.3 | 0.066 | 6.2 | 16 | 74 | 16 | >1000 | >1000 |
| AMD | 2-Naph | CO(CH$_2$)$_4$CH$_3$ | | 6.5 | 0.064 | 2.6 | 19 | 270 | 23 | >1000 | >1000 |
| AMD | 2-Naph | CO-cPr | | 0.14 | 0.044 | 5.1 | 45 | 540 | 22 | >1000 | 170 |
| AMD | 2-Naph | CO-cBu | | 2.5 | 0.026 | 7.6 | 58 | >1000 | 56 | >1000 | >1000 |
| AMD | 2-Naph | CO-cHex | | 36 | 0.072 | 10.2 | 58 | 350 | 79 | >1000 | >1000 |
| AMD | 2-Naph | CO—CH$_2$-(thienyl) | | 2.5 | 0.081 | 2.7 | 16 | 72 | 19 | >1000 | 170 |
| Ame | 2-Naph | 2-Pyl | | 24 | 0.53 | 26 | 130 | >1000 | 94 | >1000 | >1000 |

Table 2 is an overview of all the synthesized and in vitro-tested compounds which are not included in Table 1.

TABLE 2

Summary of the synthesized compounds of general formula I, not mentioned in Table 1

| $R^1$ | $R^2$ | $R^3$ | $R^1$ | $R^2$ | $R^3$ | $R^1$ | $R^2$ | $R^3$ |
|---|---|---|---|---|---|---|---|---|
| AMD(D) | 2-Naph | Ac | AMD | 2-Naph | SO$_2$CF$_3$ | AMe | 2-Naph | SO$_2$Et |
| AMD(D) | 2-Naph | EtOH | AMD | 2-Naph | SO$_2$N(Me)$_2$ | AMe | 2-Naph | SO$_2$CF$_3$ |
| AMD(D) | 2-Naph | For | AMD | 2-Naph | SO$_2$-1-Naph | AMe | 2-Naph | SO$_2$N(Me) |
| AMD | Cm | Ac | AMD | 2-Naph | TIPP | AMe | 2-Naph | SO$_2$-Ph |
| AMD(L) | Tol | Ac | AMD | 2-Naph | SO$_2$-Pmc | AMe | 2-Naph | SO$_2$-Tol |
| AMD | 2-Naph | AcONHiPr | AMD | 2-Naph | SO$_2$-(—)Cm | AMe | 2-Naph | TIPP |
| AMD | 2-Naph | SO$_2$CH(Me)$_2$ | AMD | 2-Naph | Bzl | AMe | 2-Naph | SO$_2$-2-Naph |
| AMD | 2-Naph | EtOEtOH | AMD | Tol | Ac | AMe | 2-Naph | 2-Pym |
| AMD | 2-Naph | H | AMD | TIPP | EtOH | AMe | Tol | Ac |
| AMD | 2-Naph | CH$_2$CO—N | AMD | TIPP | CON(Me)$_2$ | AMe | Mtr | Ac |
| | | | AMD | TIPP | SO$_2$Me | AMe | Mtr | SO$_2$Me |
| AMD | 2-Naph | COEt | AMD | TIPP | SO$_2$-2-Naph | AMe | Pmc | Ac |
| AMD | 2-Naph | COCH$_2$CH(Ph)$_2$ | AMD | Mtr | Ac | AMe | Pmc | EtOH |
| AMD | 2-Naph | COC(Me)$_3$ | AMD | Mtr | EtOH | AMe | Pmc | SO$_2$Me |
| AMD | 2-Naph | CO-Ph | AMD | Mtr | CON(Me)$_2$ | AMe | Pmc | 2-Pyl |
| AMD | 2-Naph | CO-Ph-OMe(p) | AMD | Mtr | SO$_2$-2-Naph | AMe | AC | Ac |
| AMD | 2-Naph | CO-(2)-Naph | AMD | 1-Naph | Ac | AMe | 2-Naph | For |
| AMD | 2-Naph | CO-CH$_2$-NH$_2$ | AMD | 1-Naph | EtOH | AMe | 2-Naph | Ac |
| AMD | 2-Naph | CO-CH$_2$NHCOCOMe | AMD(D) | Pmc | SO$_2$Me | AMe | 2-Naph | H |
| AMD | 2-Naph | CO-CH$_2$NHBoc | AMD | Pmc | SO$_2$-2-Naph | AMe | 2-Naph | COEt |
| AMD | 2-Naph | COCOOME | AMD | Pmc | 2-Pyl | AMe | 2-Naph | CON(Me)$_2$ |
| AMD | 2-Naph | CH$_2$COOMe | AMD | Cm | Ac | AMe | 2-Naph | SO$_2$Me |
| AMD(D) | 2-Naph | CO-N(Me)$_2$ | AMD | 2-Naph | CO—N(morpholino) | AMe | 2-Naph | CH$_2$CO—N(piperidino) |
| AMD | 2-Naph | CO-N(Et)$_2$ | AMD | 2-Naph | CH$_2$-cyclohexyl | | | |
| AMD(D) | 2-Naph | SO$_2$Me | | | | | | |

Tables 3–5 show the results of studies on the pharmacokinetics of representative compounds of the present invention and, for comparison, the values with NAPAP. Table 6 shows the results obtained with selected compounds after intraduodenal application. The compounds to be tested were administered to rats intravenously (Table 3), perorally (Table 4), rectally (Table 5) and intraduodenally (Table 6), respectively. After administration, blood samples were taken from the test animals at time intervals from 2 to maximally 360 minutes and the blood level of the compounds to be tested was determined by HPLC.

TABLE 3

Concentration (ng/ml) of selected compounds in the plasma of rats after intravenous administration of 1 mg/kg

| Time (min) | Compound |  |  |  |  |  |  |
|---|---|---|---|---|---|---|---|
|  | NAPAP | No. X | No. 1 | No. 2 | No. 3 | No. 5 | No. 6 |
| 5 | 1150 | 812 | 1058 | 780 | 2210 | 879 | 823 |
| 15 | 428 | 169 | 394 | 224 | 145 | 367 | 289 |
| 30 | 376 | 40 | 150 | 95 | 313 | 151 | 194 |
| 60 | 192 | 8 | 89 | 38 | 112 | 50 | 141 |
| 120 | 84 | 0 | 74 | 12 | 0 | 0 | 86 |
| 180 | 106 | 0 | 51 | 10 | 0 | 0 | 70 |

TABLE 4

Concentration (ng/ml) of selected compounds in the plasma of rats after oral administration of 50 mg/kg

| Time (min) | Compound |  |  |  |
|---|---|---|---|---|
|  | NAPAP | No. X | No. 1 | No. 2 |
| 30 | 0 | 33 | 87 | 1197 |
| 60 | 0 | 10 | 63 | 873 |
| 120 | 0 | 0 | 57 | 333 |
| 180 | 0 | 0 | 69 | 124 |
| 240 | 0 | 0 | 91 | 44 |
| 300 | 0 | 0 | 61 | 46 |

TABLE 5

Concentration (ng/ml) of selected compounds in the plasma of rats after rectal administration

| Time (min) | Dose mg/kg | NAPAP 100 | No. X 100 | No. 1 100 | No. 2 100 | No. 3 20 | No. 5* 20 | No. 6 20 |
|---|---|---|---|---|---|---|---|---|
| 30 |  | 18 | 3255 | 31406 | 32448 | 7260 | 1650 | 1179 |
| 60 |  | 0 | 2371 | 17862 | 23132 | 3800 | 958 | 449 |
| 120 |  | 0 | 1804 | 3776 | 5302 | 1740 | 299 | 850 |
| 180 |  | 0 | 898 | 1075 | 2696 | 814 | 192 | 272 |
| 240 |  | 0 | 626 | 438 | 1263 | 215 |  | 46 |
| 300 |  | 0 | 592 | 220 | 810 | 61 |  |  |
| 360 |  | 0 | 448 | 158 | 508 | 34 |  |  |

*free base of the compound

TABLE 6

Concentration (ng/ml) of selected compounds in the plasma of rats after intraduodenal administration of 100 mg/kg

| Time (min) | Compound |  |  |  |  |  |
|---|---|---|---|---|---|---|
|  | No. 2 | No. 3 | No. 3* | No. 5 | No. 5* | No. 6 |
| 30 | 21691 | 3824 | 2262 | 8744 | 1576 | 20460 |
| 60 | 15152 | 2172 | 795 | 9314 | 1900 | 6495 |
| 120 | 4275 | 1457 | 361 | 8612 | 1763 | 3284 |
| 180 | 2598 | 945 | 228 |  | 297 | 2064 |
| 240 | 2185 | 1277 | 144 |  | 530 | 1500 |
| 300 | 2195 | 1400 | 276 |  | 137 | 1203 |
| 360 | 2847 |  |  |  | 119 | 1437 |

*free base of the compound

The derivatives investigated show an improved pharmacokinetic behaviour not only in comparison to NAPAP, but also to the previously described piperazide X. Although compounds 1, 2, 3, 5 and 6 of the present invention are eliminated at comparable rate after intravenous administration and only slightly resorbed after oral application, in part very high blood levels lasting for 1 to 2 hours are found after rectal administration. After rectal administration, NAPAP cannot be detected in plasma, while some of the representative compounds tested in the present invention reach extremely high concentrations. Compounds 1, 2 and 3 can be detected in plasma even after 6 hours. The plasma levels obtained after rectal administration are considerably higher than those of the previously described piperazide X. Also the plasma concentrations measured after intraduodenal application, partly after several hours, are considerable.

In vitro, some of the representative compounds of the present invention have an extraordinary anticoagulant activity. In all cases, the thrombin time (TT) was the most prolonged value. This corresponds to the selectivity of these inhibitors which, among the clotting factors, inhibit thrombin most effectively. This is illustrated for compounds 1 to 11 in Table 7. Prolongation of the activated partial thromboplastin time (aPTT), which is also influenced, besides thrombin, by the enzymes which participate in the early phase of coagulation, is obtained by higher inhibitor concentrations. This also applies to the influence of the prothrombin time (PT) which represents the extrinsic coagulation pathway. Table 7 shows the concentrations that are necessary to double the clotting times. For the effective thrombin inhibitors 1, 2, 4, 5, 6 and 7, the value amounts to less than $10^{-7}$ mol/l for the prolongation of the TT, to 1 µmol/l for the prolongation of the aPTT and PT. The active inhibitors NAPAP and compound X tested for comparison purposes are efficient according to their $K_i$-value.

In plasma, inhibitors of the piperazine type are (absolutely) stable. Incubation in human plasma at 37° C. did not lead to any change in the inhibitory activity for 5 hours.

TABLE 7

Inhibition of coagulation in human plasma by selected compounds

| No. | Thrombin inhibition $K_i$, µmol/l | Concentr. [µmol/l] to double the | | |
|---|---|---|---|---|
| | | Thrombin time | aPTT | Prothrombin time |
| NAPAP | 0.006 | 0.048 | 0.50 | 1.0 |
| X | 0.67 | 4.1 | 20 | 45 |
| 1 | 0.023 | 0.095 | 0.90 | 2.5 |
| 2 | 0.012 | 0.055 | 0.36 | 0.90 |
| 3 | 0.036 | 0.14 | 0.65 | 1.3 |
| 4 | 0.014 | 0.085 | 1.2 | 2.0 |
| 5 | 0.0021 | 0.034 | 0.26 | 0.39 |
| 6 | 0.004 | 0.042 | 0.3 | 0.65 |
| 7 | 0.012 | 0.075 | 0.55 | 1.0 |
| 8 | 0.031 | 0.13 | 1.2 | 2.0 |
| 9 | 0.020 | 0.12 | 0.57 | 1.1 |
| 10 | 0.0053 | 0.10 | 0.44 | 0.8 |
| 11 | 0.026 | 0.22 | 1.8 | 3.1 |

The anticoagulant effect of the compounds can also be demonstrated in vivo. After rectal administration of the compounds to be tested, the anticoagulant effect was determined in the plasma of experimental animals. This is illustrated for compounds 2, 3, 5 and 6 in Table 8. Like the concentration progression determined by means of HPLC in plasma, the antithrombin effect can be detected in the clotting test.

TABLE 8

Inhibition of coagulation in rat plasma after rectal application of compounds 2, 3, 5 and 6

| Time (min) | Concentration in plasma (ng/ml) | Clotting time (sec) | |
|---|---|---|---|
| | | Thrombin time | aPTT |
| Compound 2 | 20 mg/kg | | |
| 0 | 0 | 64 | 28 |
| 30 | 5440 | >300 | 120 |
| 60 | 2090 | >300 | 87 |
| 120 | 812 | >300 | 59 |
| 180 | 660 | >300 | 50 |
| Compound 2 | 5 mg/kg | | |
| 0 | 0 | 32 | 22.5 |
| 30 | 296 | >300 | 37 |
| 60 | 160 | 224 | 33 |
| 120 | 60 | 176 | 30 |
| 180 | 40 | 107 | 26.4 |
| Compound 3 | 5 mg/kg | | |
| 0 | 0 | 45 | 23.5 |
| 30 | 897 | 300 | 39.8 |
| 60 | 462 | 298 | 32.8 |
| 120 | 355 | 165 | 27.4 |
| 180 | 49 | 114 | 26.0 |
| Compound 5 | 20 mg/kg | | |
| 0 | 0 | 153 | 22 |
| 30 | 1572 | >300 | 65 |
| 60 | 983 | >300 | 62.5 |
| 120 | 380 | >300 | 36 |
| 180 | 195 | >300 | 29.7 |

TABLE 8-continued

Inhibition of coagulation in rat plasma after rectal application of compounds 2, 3, 5 and 6

| Time (min) | Concentration in plasma (ng/ml) | Clotting time (sec) | |
|---|---|---|---|
| | | Thrombin time | aPTT |
| Compound 5 | 5 mg/kg | | |
| 0 | 0 | 51.5 | 21.2 |
| 30 | 168 | >300 | 34.5 |
| 60 | 65 | 255 | 30.5 |
| 120 | 82 | 137.5 | 27.5 |
| 180 | 10 | 95 | 25.3 |
| Compound 6 | 5 mg/kg | | |
| 0 | 0 | 55.3 | 22.3 |
| 30 | 648 | >300 | 34.5 |
| 60 | 362 | >300 | 31.5 |
| 120 | 157 | >300 | 28.4 |
| 180 | 83 | 213 | 26 |

After rectal application, the compounds of the present invention are absorbed to an extent leading to antithrombotically active plasma levels. This has been shown with the model of the stasis-induced venous thrombosis in the rat according to Wessler et al. This method consisted in macroscopically evaluating thrombi induced by serum in jugular vein segments by means of a scale (0=liquid blood, 1=one or several small thrombi, 2=not fully closed vascular segment, 3=fully closed vascular segment). The antithrombotic effect is clearly dose-dependent. At a dose of 100 or 20 mg/kg, respectively, the thrombus formation is completely inhibited; at the lower dose of 5 mg/kg, vascular occlusion is largely prevented or thrombus formation is greatly enhanced, respectively.

TABLE 9

Dose-dependent antithrombotic efficacy after rectal application of compound 2 on the model of stasis-induced venous thrombosis in the rat

| Dose (mg/kg) | n | Plasma level (ng/ml) | | Thrombus scale | | | | relative thrombus scale |
|---|---|---|---|---|---|---|---|---|
| | | 30 min | 60 min | 0 | 1 | 2 | 3 | |
| 0 | 5 | 0 | 0 | 0 | 0 | 1 | 9 | 1 |
| 100 | 3 | 28698 | 16118 | 6 | 0 | 0 | 0 | 0 |
| 20 | 4 | 1617 | 998 | 6 | 1 | 0 | 0 | 0.05 |
| 5 | 5 | 228 | 160 | 0 | 8 | 2 | 0 | 0.41 | n = number of experimental animals each having generally 2 vein segments evaluated.

The relative thrombus scale is the quotient of the mean thrombus size of the treated group (e.g. the mean value at 5 mg/kg is 1.2) and the mean thrombus size of the control group (2.9).

The piperazides synthesized according to the method described in the present invention and used as such or as salts with a physiologically compatible mineral or organic acid can be converted in appropriate forms of application by applying adequate auxiliaries and carriers. Corresponding to the pharmacological behaviour, tablets, dragées, suppositories and solutions are particularly significant.

The dosage depends above all on the antithrombin activity, the attainable blood level with the corresponding form of application, the bioavailability as well as the patient's general constitution, whereby a sufficient antithrombotic activity can be reached with dosages between 0.5 and 50 mg/kg.

By means of Nα-(2-naphthylsulfonyl)-(L)-3-amidinophenylalanine-4-acetylpiperazide hydrochloride (compound 2), the conversion into 3 pharmaceutical forms of administration should be representatively shown.

EXAMPLE 1

Tablets with 20 mg of compound 2 as the active substance, coated with a gastric juice-resistant protective lacquer
Composition: Core: 20 mg of active substance, 96 mg of lactose, 3 mg of talcum and 1 mg of magnesium stearate. Coating: 23.92 mg of Eudragit S 12.5 P (Röhm Pharma, Darmstadt), 0.266 mg of dibutylphthalate, 0.744 mg of talcum, 23.92 mg of acetone/ethanol 1+1.
Manufacturing process: The active substance mixed with the additives is pressed through a 0.5 mm-meshed sieve and, once dried, formed into oval tablet cores. The protective lacquer is then sprayed in a special granulator, whereupon the lacquered cores are dried.

EXAMPLE 2

Suppositories with 10 mg of compound 2 as the active substance.
Composition: 1 suppository contains 10 mg of active substance and 1 g of Witepsol W45 as the basic substance.
Specifications for the manufacture of 10 suppositories: 100 mg of the finely powdered active substance are ground with the liquefied basic substance. The preparation is mixed portionwise with the remaining liquefied basic substance and worked until a regular quality is obtained. Nearly at the limit of pourability, the mixture is poured in an adequate form and allowed to cool down at rest.

EXAMPLE 3

Injection and infusion solution, respectively, with 2.5 mg/ml of compound 2 as the active substance.
Manufacturing process: 0.25 g of active substance is diluted in 100 ml of water for injection, whereafter the solution is filtered and, if necessary, filled into 2 ml ampoules. The closed containers filled with this solution (infusion bottles, ampoules) are submitted to a steam sterilization at 121° to 124° C.

We claim:
1. D,L-, L- or D-phenylalanine piperazides of formula

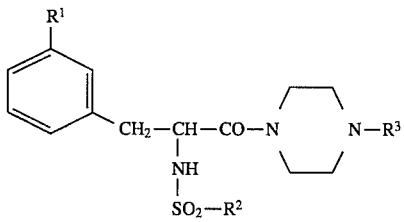

I wherein
$R^1$ represents a basic group of formula

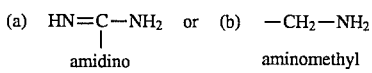

$R^2$ represents an (un)substituted aryl or heteroaryl residue, and
$R^3$ represents an acyl residue of formula —COX, wherein X=H, unbranched or branched, possibly substituted alkyl, or (un)substituted aryl or cycloalkyl,
an aralkyl residue in which the aromatic residue may be substituted,
a carboxamide residue of formula —CONR'R", a thiocarboxamide residue of formula —CSNR'R" or an ethylamide residue of formula —CH$_2$—CONR'R" in which R'=R"=H; R'=R"=alkyl; R'=H, R"=alkyl; R'=H, R"=aryl, or R' and R" may form a cycloaliphatic or heterocycloaliphatic ring with the nitrogen atom,
an SO$_2$—Y residue in which Y means (un)substituted alkyl, (un)substituted aryl or heteroaryl or —NR'R", in which R' and R"=H may be equal or not to low alkyl $C_{1-C3}$,
a cycloaliphatic ring with 5 to 8 C atoms which may be substituted with a hydroxyl or oxo group,
an (un)substituted heteroaryl residue or a heterocycloaliphatic residue, respectively,
a functionalized alkyl residue of formula —(CH$_2$)$_n$—X wherein the alkyl chain may be unbranched or branched, n=1 to 8 and the functional residue X represents
a hydroxyl group the H atom of which can be substituted,
a halogen atom,
a tertiary amino group of formula —N(Alk)$_2$ wherein the alkyl groups have 1 to 3 C atoms, and the alkyl groups are same, and the nitrogen atom may belong to a cycloaliphatic ring with 5 to 7 ring parts to which one or two further rings may be added,
an acylaminomalonate group of formula

an

group or a

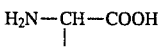

group,
and the salts thereof with mineral or organic acids.

2. Phenylalanine piperazides according to claim 1, wherein the (un)substituted aryl or heteroaryl residue in $R^2$ represents phenyl, 4-methylphenyl, 2,4,6-trimethyl- or -triisopropylphenyl, 4-methoxy-2,3,6-trimethylphenyl, 2,2-dimethyl-6-methoxy- or 2,2,5,7,8-pentamethylchromanyl, anthraquinonyl, 1- or 2-naphthyl, quinolyl- or isoquinolyl, or a camphor residue, respectively.

3. Phenylalanine piperazides according to claim 1, wherein X in the acyl residue in $R^3$ is lower alkyl or cycloalkyl.

4. Phenylalanine piperazides according to claim 1, wherein the aromatic residue of the aralkyl residue in $R^3$ is substituted with a halogen atom, an alkyl, alkoxy, hydroxy or nitro group.

5. Phenylalanine piperazides according to claim 1, wherein the alkyl residue in the SO$_2$—Y residue is methyl, trifluoromethyl or trichloromethyl.

6. Phenylalanine piperazides according to claim 1, wherein the aryl or heteroaryl residue in the SO$_2$—Y residue is phenyl, 4-methylphenyl, 2,4,6-trimethyl- or -triisopropylphenyl, 4-methoxy-2,3,6-trimethylphenyl, 2,2-dimethyl-6-methoxy- or 2,2,5,7,8-pentamethylchromanyl, anthraquinonyl, naphthyl or quinolyl, or O-aryl, respectively.

7. Phenylalanine piperazides according to claim 1, wherein the (un)substituted heteroaryl residue in $R^3$ is pyridyl or pyrimidyl, or the heterocycloaliphatic residue in $R^3$ is N-methylpiperidyl, respectively.

8. Phenylalanine piperazides according to claim 1, wherein the H atom of the hydroxyl group in the functionalized alkyl residue in $R^3$ is substituted with an alkyl, aralkyl, aryl, hydroxyalkyl or acyl group.

9. Phenylalanine piperazides according to claims 1, wherein Ac in the acylaminomalonate group of formula AcHN—C(COOAlk)$_2$ and in the AcHN—CH—COOH group of the functionalized alkyl residue means formyl or acetyl and Alk=low alkyl $C_1$—$C_3$.

10. Phenylalanine piperazides according to claim 1, wherein $R^1$ represents a basic group of formula (a)=amidino, $R^2$ means a β-naphthyl, anthraquinone, 2,4,6-triisopropylphenyl or 2,2,5,7,8-pentamethylchroman group, and $R^3$ represents an acyl residue, a functionalized alkyl residue, an $SO_2$—Y residue, a carboxyamide residue or heteroaryl residue.

11. The phenylalanine piperazides according to claim 3, wherein X in the acyl residue in $R^3$ is methyl or $C_3$ to $C_{10}$ cycloalkyl.

12. The phenylalanine piperazides according to claim 10, wherein $R^3$ is formyl, acetyl, 2-hydroxyethyl, 2-pyridyl, or 2-pyrimidyl.

13. Method for the synthesis of phenylalanine piperazides according to claim 1, which comprises converting a (D,L)-3-cyanophenylalanine alkylester of formula II

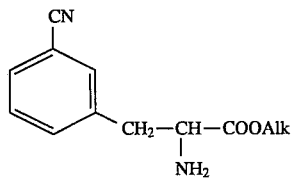

with a sulfochloride $R^2$—$SO_2Cl$, wherein $R^2$ has the denotation given in claim 1 or 2, into a racemic compound of formula IV

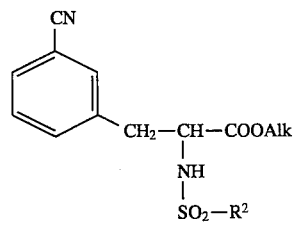

from which racemates of the sulfonylated cyanophenylalanines of formula V

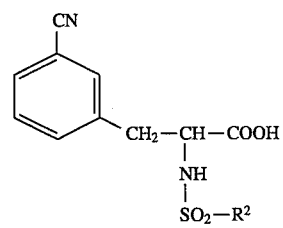

are obtained by hydrolysis, or converting the compounds of formula IV by enzymatic ester hydrolysis with chymotrypsin into the L-configurated amino acids of formula V and converting the D-configurated amino alkyl carboxylates of formula IV obtained by the enzymatic ester hydrolysis into the D-configurated amino carboxylic acids of formula V by hydrolysis, converting the compounds of formula V by coupling with a piperazine derivative of formula VII

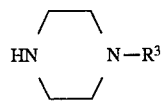

into the (D,L)-, D- or L-cyano compounds with piperazide structure of formula VI

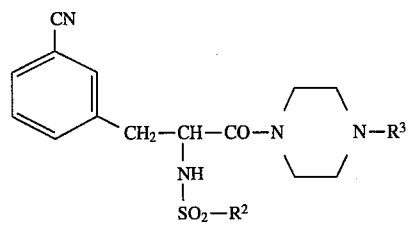

synthesizing the thioamide of formula VIII

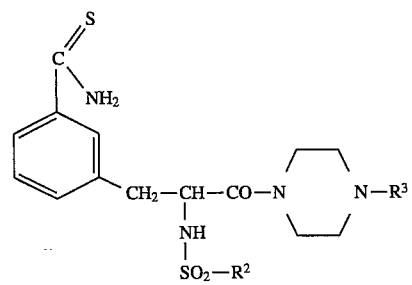

by addition of $H_2S$ to the cyano function, synthesizing a thioimidate halide of formula IX

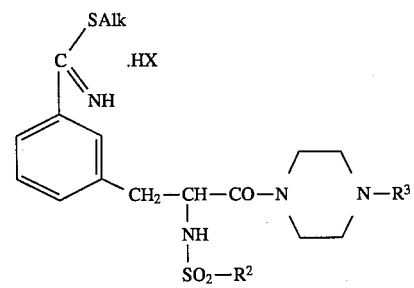

by conversion with an alkyl halide, or synthesizing the imidate halides of formula X

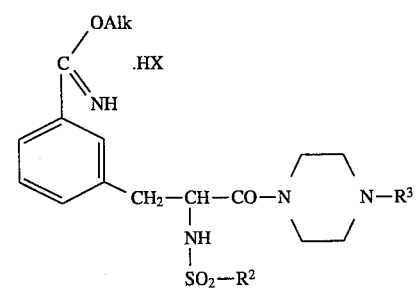

from the cyano compounds with piperazide structure of formula VI, and converting the compound of formula IX with ammonium acetate or the compound of formula X in an alcoholic ammonia solution into compounds of formula XI

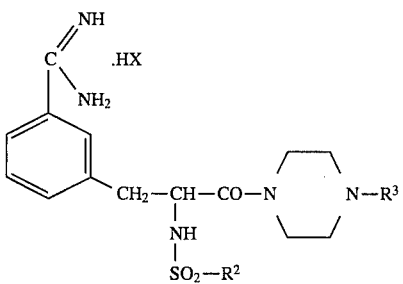

wherein X means halogen, preferentially chlorine.

14. The method of claim 13, further comprising converting the compounds of formula IX with ammonium acetate into compounds of formula XI, wherein X is chloride.

15. A method of achieving an anticoagulant or anti-thrombin induced coagulation effect in a subject, comprising, administering to a subject a pharmaceutically effective dosage of at least one of the phenylalanine piperazides according to claim 1 in the form of a pharmaceutically acceptable salt or free base, thereby producing an anticoagulant or anti-thrombin induced coagulation effect in the subject.

16. The method of claim 15, further comprising administering at least one phenylalanine piperazide in the form of an antithrombotically active drug subcutaneously, intravenously, orally, rectally, or intraduodenally.

17. Antithrombotically active drug to be administered subcutaneously or intravenously, orally, rectally, or duodenally, in which an efficient quantity of at least one phenylalanine piperazide according to claim 1 and appropriate additives are present.

18. Antithrombotically active drug according to claim 17, in the form of tablets, dragées, capsules, pellets, suppositories, solutions, injections or transdermal systems.

19. Method for blood coagulation or thrombin or trypsin inhibition, in living organisms, characterized by the administration of an effective quantity of a phenylalanine piperazide according to claim 1 or of an antithrombotically active drug according to claim 17 or 18.

* * * * *